United States Patent
Dowaki et al.

(10) Patent No.: US 8,934,094 B2
(45) Date of Patent: Jan. 13, 2015

(54) METHOD OF MEASURING RAMAN SCATTERED LIGHT, AND CONTAINER FOR RAMAN SCATTERED LIGHT MEASUREMENT SPECIMEN

(71) Applicant: Sony Corporation, Tokyo (JP)

(72) Inventors: Suguru Dowaki, Kanagawa (JP); Kazuhiro Nakagawa, Saitama (JP); Eriko Matsui, Tokyo (JP)

(73) Assignee: Sony Corporation, Tokyo (JP)

( * ) Notice: Subject to any disclaimer, the term of this patent is extended or adjusted under 35 U.S.C. 154(b) by 17 days.

(21) Appl. No.: 13/757,411

(22) Filed: Feb. 1, 2013

(65) Prior Publication Data

US 2013/0222798 A1   Aug. 29, 2013

(30) Foreign Application Priority Data

Feb. 24, 2012  (JP) .................................. 2012-038887

(51) Int. Cl.
*G01J 3/44*      (2006.01)
*G01N 21/65*    (2006.01)

(52) U.S. Cl.
CPC .. *G01J 3/44* (2013.01); *G01N 21/65* (2013.01)
USPC .......................................... 356/301; 356/246

(58) Field of Classification Search
USPC ................ 356/244, 246, 301, 319, 326, 328; 600/316, 342, 327, 341
See application file for complete search history.

(56) References Cited

U.S. PATENT DOCUMENTS

| | | | |
|---|---|---|---|
| 7,288,419 B2 * | 10/2007 | Naya ............................... | 438/20 |
| 7,460,224 B2 * | 12/2008 | Wang et al. .................... | 356/301 |
| 2004/0183176 A1 * | 9/2004 | Naya et al. .................... | 257/680 |
| 2006/0044554 A1 * | 3/2006 | Mertz et al. ................... | 356/246 |
| 2007/0013907 A1 * | 1/2007 | Pobortchi et al. ............. | 356/301 |
| 2009/0273780 A1 * | 11/2009 | Tomaru et al. ................ | 356/301 |
| 2010/0296086 A1 * | 11/2010 | Wang et al. .................... | 356/301 |

FOREIGN PATENT DOCUMENTS

| | | |
|---|---|---|
| JP | 2005-532547 | 10/2005 |
| JP | 2006-300611 | 11/2006 |

* cited by examiner

*Primary Examiner* — Hoa Pham
(74) *Attorney, Agent, or Firm* — K&L Gates LLP

(57) ABSTRACT

The present disclosure provides a method of measuring a Raman scattered light which is capable of detecting a Raman scattered light derived from a specimen at a high sensitivity, and a container for a Raman scattered light measurement specimen for use therein. The method of measuring a Raman scattered light includes radiating an exciting light to a specimen on a sheet member made of a material different from a material of an accommodating section and disposed within the accommodating section, thereby detecting a Raman scattered light.

15 Claims, 8 Drawing Sheets

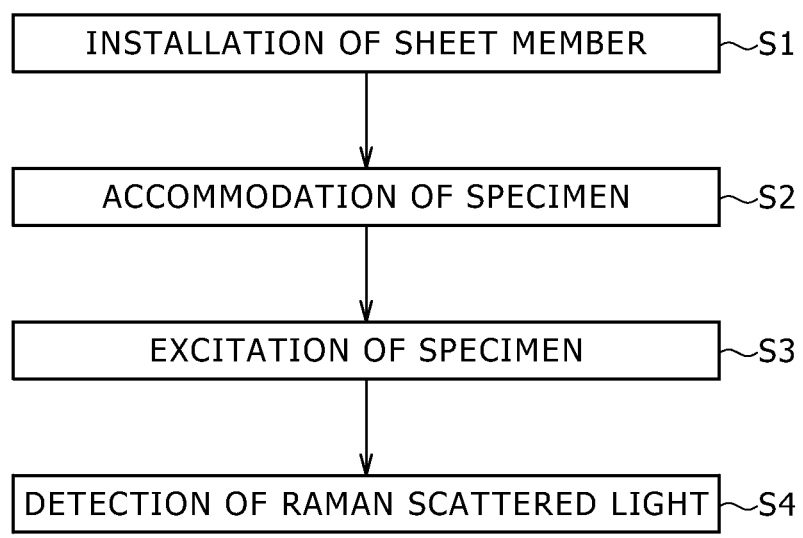
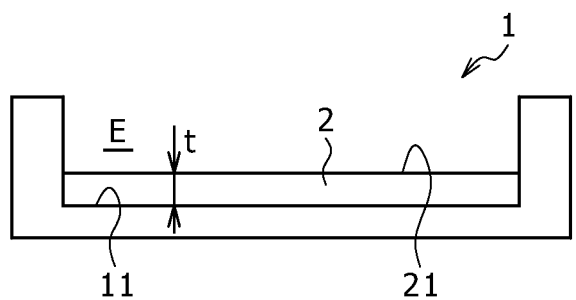

FIG.3
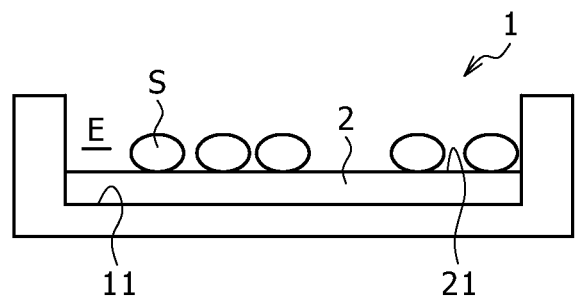
FIG.4
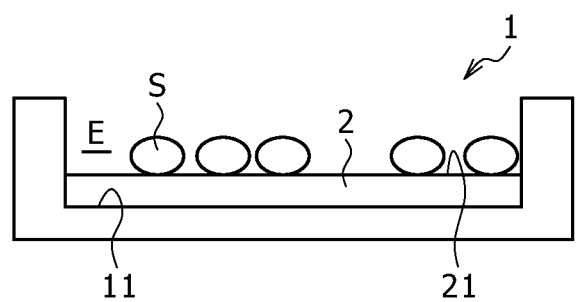
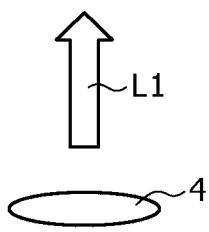
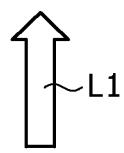

METHOD OF MEASURING RAMAN SCATTERED LIGHT, AND CONTAINER FOR RAMAN SCATTERED LIGHT MEASUREMENT SPECIMEN

CROSS REFERENCES TO RELATED APPLICATIONS

The present application claims priority to Japanese Priority Patent Application JP 2012-038887 filed in the Japan Patent Office on Feb. 24, 2012, the entire content of which is hereby incorporated by reference.

BACKGROUND

The present disclosure relates to a method of measuring a Raman scattered light and a container for a Raman scattered light measurement specimen. More particularly, the present disclosure relates to a method of measuring a Raman scattered light which is capable of detecting a Raman scattered light derived from a specimen at a high sensitivity, and a container for a Raman scattered light measurement specimen for use therein.

When a light is radiated to a material, in addition to a scattered light having the same wavelength as that of the radiated light, lights having wavelengths each different from that of the radiated light emitted from the material are generated. The reason for this is because molecules contained in the material are excited to a vibrational-excited state due to the radiated light, whereby a part of energy of the radiated light is transferred to the molecules and thus the wavelength of the radiated light is changed. A scattered light whose wavelength is changed to wavelengths each different from that of the radiated light is referred to as "a Raman scattered light." The degree of shifting of the wavelength in the Raman scattered light is based on a vibration inherent in the molecules contained in the material to which the light is radiated. Therefore, the Raman scattered light is detected, an intensity is measured every wavelength, and the resulting Raman spectrum is analyzed, whereby it is possible to identify the molecules contained in the material, and a state of the material.

An analysis object in an analyzing method utilizing the Raman spectrum includes many things such as a polymer material, a metallic compound, and a semiconductor. In recent years, the analysis utilizing the Raman scattered light has been carried out for a biological specimen such as a tissue or a cell derived from the human.

As the analysis for the biological specimen based on the Raman spectrum, for example, a technique for utilizing that analysis in the clinical diagnosis is disclosed. With a technique disclosed in Japanese Patent Laid-Open No. 2006-300611, data on the Raman spectra obtained from a cancer tissue and a normal tissue of the human is collected, standard data is created with respect to various kinds of tissues, and the diagnosis for the cancer is carried out based on the standard data.

Also, in addition to the clinical diagnosis, there is also disclosed a technique for utilizing the Raman spectrum in the analysis for a cultured cell as the biological specimen. For example, with a technique disclosed in JP-T-2005-532547, with regard to a change, such as cell division or apoptosis, generated in the cultured cell, the Raman spectra derived from the respective cultured cells are analyzed, thereby analyzing the changes in the cells.

SUMMARY

The present disclosure has been made in order to solve the problems described above, and it is therefore desirable to provide a method of measuring a Raman scattered light which is capable of detecting a Raman scattered light derived from a specimen at a high sensitivity, and a container for a Raman scattered light measurement specimen for use therein.

In order to attain the desire described above, according to an embodiment of the present disclosure, there is provided a method of measuring a Raman scattered light, the method including: radiating an exciting light to a specimen on a sheet member made of a material different from a material of an accommodating section and disposed within the accommodating section, thereby detecting a Raman scattered light.

According to another embodiment of the present disclosure, there is provided a container for a Raman scattered light measurement specimen, the container including: an accommodating section in which a specimen is accommodated; and a sheet member made of a material different from a base material of a bottom surface of the accommodating section, and provided on the bottom surface.

The Raman scattered light is detected at a higher sensitivity in the measurement of the specimen accommodated in the container by utilizing the method of measuring a Raman scattered light, and the container for a Raman scattered light measurement specimen according to the embodiments of the present disclosure.

As set forth hereinabove, according to the present disclosure, there are provided the method of measuring a Raman scattered light which is capable of measuring the Raman scattered light derived from the specimen at the high sensitivity, and the container for a Raman scattered light measurement specimen for use therein.

Additional features and advantages are described herein, and will be apparent from the following Detailed Description and the figures.

BRIEF DESCRIPTION OF THE FIGURES

FIG. 1 is a flowchart explaining procedures of a method of measuring a Raman scattered light according to a first embodiment of the present disclosure;

FIG. 2 is a schematic cross sectional view explaining a procedure for installing a sheet member on a bottom surface of a container;

FIG. 3 is a schematic cross sectional view explaining a procedure for accommodating a specimen in the container;

FIG. 4 is a schematic cross sectional view, partly in block, explaining a procedure for exciting the specimen;

DETAILED DESCRIPTION

Figure 5:
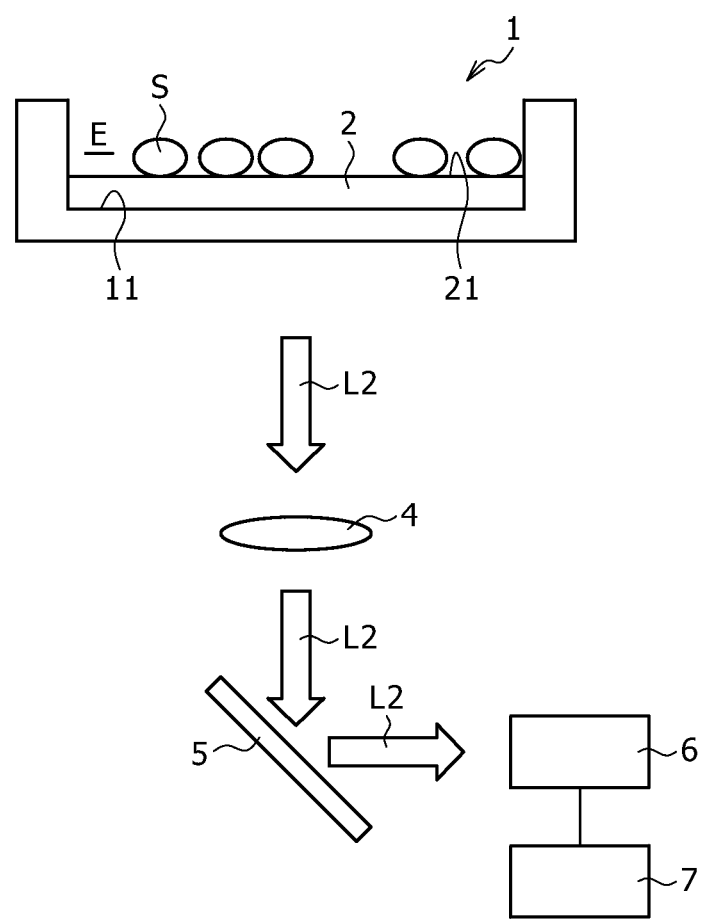
FIG. 5 is a schematic cross sectional view, partly in block, explaining a procedure for detecting a Raman scattered light emitted from the specimen.

Embodiments of the present disclosure will be described in detail hereinafter with reference to the accompanying drawings. It is noted that the embodiments which will be described below show representative embodiments of the present disclosure, and thus the scope of the present disclosure is not intended to be construed in a limiting sense by the embodiments. The description will be given below in accordance with the following order.

1. Preparation of Specimen in Method of Measuring Raman Scattered Light According to First Embodiment of the Present Disclosure
(1-1) Installation of Sheet Member
(1-2) Accommodation of Specimen
2. Measurement of Specimen in Method of Measuring Raman Scattered Light According to First Embodiment of the Present Disclosure
(2-1) Excitation of Specimen
(2-2) Detection of Raman Scattered Light
3. Container for Raman Scattered Light Measurement Specimen According to Second Embodiment of the Present Disclosure
4. Examples

1. Preparation of Specimen In Method of Measuring Raman Scattered Light According to First Embodiment of the Present Disclosure A method of measuring a Raman scattered light according to a first embodiment of the present disclosure will now be described with reference to a flow chart shown in FIG. 1. Procedures S1 to S4 shown in FIG. 1 can be classified into two stages: preparation of a specimen; and a measurement of the specimen. Firstly, a description will now be given with respect to the installation of a sheet member (S1) and accommodation of the specimen (S2) as the procedure as the preparation of the specimen.

(1-1) Installation of Sheet Member

In FIG. 1, reference symbol S1 designates a procedure for installing a sheet member on a bottom surface of a container for a Raman scattered light measurement specimen (hereinafter referred to as "a container for a specimen" as well) as a container in which a specimen as an object of a measurement of a Raman scattered light is accommodated in a phase of the measurement. FIG. 2 shows the container for a specimen which is used in the method of measuring a Raman scattered light according to the first embodiment of the present disclosure. A container 1 for a specimen has therein a space E for accommodation of the specimen. In the procedure S1, a sheet member 2 made of a material different from a base material of a container bottom surface 11 is installed on the container bottom surface 11 contacting the space E.

Preferably, the sheet member 2 has a light permeability for the purpose of detecting a Raman scattered light which will be described later. In addition, preferably, for the purpose of detecting the Raman scattered light derived from the specimen at a higher sensitivity, the sheet member 2 is made of a material in which either an intensity of the Raman scattered light emitted is not higher than that of the Raman scattered light derived from the specimen, or a spectrum of the Raman scattered light emitted does not overlap a Raman spectrum derived from the specimen.

The sheet member 2, for example, may also be made of a synthetic resin. Preferably, a material, such as a benzene ring, which does not have a structure with which the Raman scattered light is emitted is used as the synthetic resin. The synthetic resin having such a feature includes an acrylic resin, an olefin system resin, a silicon system resin, and the like. Specifically, the synthetic resin having such a feature includes polyethylene, polypropylene, a polymethylmethacrylate resin, polydimethylsiloxane, and the like. In particular, polydimethylsiloxane is preferable. In addition, a material having elasticity may be used in the sheet member 2.

As the material of the sheet member 2, for example, when a measurement object is a biological specimen, the sheet member 2 is preferably made of a material which does not contain amide. No amide is contained in the sheet member 2, which results in that the Raman spectrum derived from the sheet member 2 and the Raman spectrum derived from the specimen do not overlap each other, and thus the Raman spectrum derived from the specimen can be measured at a higher sensitivity. The material not containing therein amide, for example, includes polysaccharide, a sugar chain, and a fat. Specifically, the material not containing therein amide, for example, includes agarose, cellulose, a hyaluronic acid, and the like.

As the material of the sheet member 2, in addition to the materials described above, a gel-like material is also preferable. The spectra converge with the Raman scattered lights which have the respective wavelengths and in which the structure is reflected, and thus the Raman scattered light can be measured at a high intensity as the structure of the material emitting the Raman scattered light has the higher regularity. In a word, the intensities of the wavelengths represented by the Raman spectra are reduced and the inhibition for the measurement of the Raman scattered light derived from the specimen is reduced in the gel-like material in which the bonding state of the molecules has the lower regularity rather than other materials described above.

The gel-like material is composed of a liquid component and a gelling component for holding the liquid component. In this case, however, the gelling component contained in the sheet member 2 includes a polyacrylic acid as synthetic polymer, a protein composing an extracellular matrix such as collagen or gelatin, and polysaccharide such as agarose.

In the method of measuring a Raman scattered light according to the first embodiment of the present disclosure, it is also preferable to use the sheet member 2 in an amorphous state. In the embodiment of the present disclosure, the amorphous is defined as a material state in which atoms, molecules or the like composing a solid do not have three-dimensionally the low regularity, and thus do not have a crystal structure. It is preferable to use a material in which the symmetry and regularity of the molecular structure are collapsed like the gel-like material described above, a material in a swelling state or a material having elasticity, including the material in the amorphous state in the sheet-like member 2.

It is only necessary that the material of the sheet member 2 in the method of measuring a Raman scattered light according to the first embodiment of the present disclosure is selected from the materials having the features described above so as to correspond to the specimen accommodated in the container 1 for a specimen. For example, when the specimen is an adhesive cultured cell, from a reason of the adhesiveness or the like between a sheet member surface 21 and the cell, a protein composing an extracellular matrix such as collagen may be selected as the sheet member 2. In addition, for the purpose of enhancing the adhesiveness between the sheet member 2 made of a synthetic resin, and the cell, a protein composing an extracellular matrix may be laminated on the sheet member surface 21.

Even in the case of the sheet member 2 made of any of the materials described above, for reducing the detection of the Raman scattered light derived from the container 1 for a specimen, preferably, a thickness t of the sheet member 2 is equal to or larger than 0.5 mm. In addition, when in addition to the measurement of the Raman scattered light, the specimen needs to be optically observed, preferably, a total thickness of the base material composing the container bottom surface 11 of the container 1 for a specimen, and the sheet member 2 is set to the degree that a correction range of a correction collar included in an objective lens 4 (refer to FIG. 4) is not exceeded. When the thickness of the sheet member 2 is smaller than the above correction range of the correction collar, it becomes difficult to reduce the Raman scattered light derived from the container 1 for a specimen which will be described later. On the other hand, when the total thickness of the base material composing the container bottom surface 11 of the container 1 for a specimen, and the sheet member 2 exceeds the correction range of the correction collar, spherical aberration is generated in the observation of the specimen and the resulting observed image becomes smudgy.

All it takes is that with regard to the container 1 for a specimen in which the sheet member 2 is installed, at least the container bottom surface 11 on which the sheet member 2 is installed is made of a material having the light permeability. Thus, a material, such as a glass or a synthetic resin, which is widely, generally used in the container can be used as the material of the container bottom surface 11. For example, when the biological specimen is measured, the container 1 for a specimen made of a synthetic resin which is easy to use as disposable use is preferable from the fear of infection of a pathogen or the like.

Note that, although in the container 1 for a specimen shown in FIG. 2, one space E for accommodation of the specimen is shown, the container for a Raman scattered light measurement specimen according to a second embodiment of the present disclosure which will be described later is by no means limited thereto. That is to say, a construction may also be adopted such that plural spaces E are provided in one container 1 for a specimen, or the sheet members 2 made of different materials may be installed on the respective container bottom surfaces 11.

The installation of the sheet member 2 on the container bottom surface 11 can be carried out through the application of the sheet member 2. When a protein composing an extracellular matrix such as collagen is used in the sheet member 2, a liquid solution containing therein a protein, for example, may be dropped to be flowed into the space E, the container 1 for a specimen may be stationarily stood, and the sheet member 2 may be adhered to the container bottom surface 11. In addition, when the synthetic resin such as PDMS is used in the sheet member 2, the synthetic resin may be polymerized in the space E and may be then laminated on the container bottom surface 11. In addition thereto, the sheet member 2 may be made in the form of a different member and, for example, may be then fitted into the space E to be installed. It is only necessary that a method of installing the sheet member 2 is selected from the known methods so as to correspond to the selected materials of the sheet member 2 and the container 1 for a specimen.

(1-2) Accommodation of Specimen

In FIG. 1, reference symbol S2 designates a procedure for accommodating the specimen in the space E within the container 1 for a specimen. FIG. 3 shows a state in which a specimen S is accommodated in the container 1 for a specimen in accordance with the procedure S2.

As shown in FIG. 3, the sheet member 2 which has been installed in accordance with the procedure S1 is laminated on the container bottom surface 11 in the container 1 for a specimen. The specimen S as an object of the measurement of the Raman scattered light is accommodated in the space E of the container 1 for a specimen, and a part of the specimen S contacts the sheet member surface 21. As a result, with regard to the specimen S, the Raman scattered light can be measured in a portion which is located at a distance of the thickness t (refer to FIG. 1) of the sheet member 2 from the container bottom surface 11 of the container 1 for a specimen.

The specimen S in the method of measuring a Raman scattered light according to the first embodiment of the present disclosure may be any of an organic material or an inorganic material. The state of the specimen S may be any of a solid, a liquid, or a mixing state of the solid and the liquid. As the object of the measurement, for example, a biological specimen is preferable, and especially, a cultured cell is more preferable.

When the specimen S is a cultured cell, as the accommodating procedure in the procedure S2 in the method of measuring a Raman scattered light according to the first embodiment of the present disclosure, the cells are seeded on the sheet material surface 21, and the culture is carried out in the space E of the container 1 for a specimen. Although an illustration is omitted in FIG. 3, for the culture of the cells, the space E may be filled with a culture solution. For the cells becoming the moment at which the Raman scattered light is to be measured, the Raman scattered light can be measured without changing the container to another one because the cells are cultured in the container 1 for a specimen. That is to say, the Raman scattered light in the living cells can be measured by using the container 1 for a specimen.

In the method of measuring a Raman scattered light according to the first embodiment of the present disclosure, the cell to be measured may be any of an adhesive cell or a suspended cell. Also, the known method is used as a method for the culture within the container 1 for a specimen, and thus the culture solutions, the culture temperatures, and the like which are suitable for the cultured cells may be selected. Although an illustration is omitted in FIG. 3, after the specimen S such as the cultured cell has been accommodated in the container 1 for a specimen, for the purpose of preventing the cultured cell from being contaminated, a cover may be put on the container 1 for a specimen.

It is noted that in the method of measuring a Raman scattered light according to the first embodiment of the present disclosure, a procedure can also be adopted such that the procedure S1 shown in FIG. 1 is omitted, the container 1 for a specimen in which the sheet member 2 is previously installed is gotten, and thus the method concerned is started from the procedure S2.

2. Measurement of Specimen in Method of Measuring Raman Scattered Light According to First Embodiment of the Present Disclosure Next, a description will now be given with respect to the excitation (S3) of the specimen, and the detection (S4) of the Raman scattered light as the procedure for measuring the specimen shown in FIG. 1.

(2-1) Excitation of Specimen

In FIG. 1, reference symbol S3 designates a procedure for radiating an exciting light L1 to the specimen S accommodated in the container 1 for a specimen, thereby exciting the specimen S. FIG. 4 shows a state in which the exciting light L1 emitted from a light source 3 and indicated by an arrow mark is transmitted through an objective lens 4 to be radiated to the specimen S, thereby exciting the specimen S in accordance with the procedure S3. In the method of measuring a Raman scattered light according to the first embodiment of the present disclosure, the specimen S is used in the measurement in a state in which it is accommodated in the container 1 for a specimen. A wavelength and an output level of the exciting light L1 radiated from the light source 3 may be both arbitrary, and thus it is only necessary to set both of the wavelength and the output level of the exciting light L1 thus radiated so as to correspond to the property of the specimen S and the performance of the light source 3.

(2-2) Detection of Raman Scattered Light

In FIG. 1, reference symbol S4 designates a procedure for detecting the Raman scattered light emitted from the specimen S accommodated in the container 1 for a specimen. Also, FIG. 5 shows a state in which a Raman scattered light L2 emitted from the specimen S is detected by using a detector 7 in accordance with the procedure S4.

In the method of measuring a Raman scattered light according to the first embodiment of the present disclosure, the Raman scattered light L2 emitted from the specimen S is transmitted through both of the sheet member 2 provided in the container 1 for a specimen in which the specimen S is accommodated, and the container bottom surface 11 to be made incident to the objective lens 4. At this time, a focal point of the objective lens 4 is focused on the specimen S. The Raman scattered light L2 thus made incident thereto is condensed by the objective lens 4, and is reflected by a beam splitter 5 to be made incident to a spectroscope 6. The spectroscope 6 includes a spectroscopic element such as a diffraction grating or a prism, and spectrally diffracts the Raman scattered light L2 thus made incident thereto in correspondence to a wavelength(s) thereof. The Raman scattered light L2 which have been spectrally diffracted every wavelength thereof is made incident to the detector 7. The detector 7 detects the Raman scattered light L2 thus spectrally diffracted to obtain a Raman spectrum. Note that, in FIGS. 4 and 5, the exciting light L1 is radiated from the bottom side of the container 1 for a specimen, and the Raman scattered light L2 emitted from the bottom side of the container 1 for a specimen is detected. However, in the method of measuring a Raman scattered light according to the first embodiment of the present disclosure, the exciting light L1 may be radiated from the upper side of the container 1 for a specimen to the specimen S, and the Raman scattered light L2 emitted from the upper side of the container 1 for a specimen and derived from the specimen S may also be detected.

In the method of measuring a Raman scattered light according to the first embodiment of the present disclosure, as described above, the specimen S is measured in a state in which the specimen S is held in the position away from the container bottom surface 11 by using the sheet member 2. When the focal point of the objective lens 4 is focused on the specimen S, by the installation of the sheet member 2, the position of the focal point is made away from the container 1 for a specimen as compared with the case where no sheet member 2 is provided. For this reason, the container bottom surface 11 of the container 1 for a specimen is made away from the vicinity of the focal point of the objective lens 4. As a result, the detection intensity of the Raman scattered light derived from the container 1 for a specimen is reduced.

In addition thereto, in the container 1 for a specimen, the sheet member 2 contacting the specimen S instead of the container bottom surface 11 is made of the material which does not impede the detection of the Raman scattered light derived from the specimen S. If the material of the sheet member 2, for example, is the synthetic resin not containing therein a benzene ring, the Raman scattered light having the high intensity is hard to emit. Also, if the sheet member 2 is made of polysaccharide, a sugar chain or a fat, when the specimen S is the biological specimen or the like, the Raman spectrum overlapping the Raman spectrum derived from the specimen S is hard to measure. In addition, even when the sheet member 2 is made of the gel-like material, the Raman scattered light having the high intensity is hard to emit. The Raman scattered light is emitted only at the lower intensity than that of the Raman scattered light emitted from the container 1 for a specimen from the sheet member 2 made of such a material. Or, the spectrum overlapping the Raman spectrum as the object of the analysis is not measured in the sheet member 2. As a result, in the method of measuring a Raman scattered light according to the first embodiment of the present disclosure, the intensity of the Raman scattered light derived from the container 1 for a specimen is reduced, and thus the Raman scattered light L2 derived from the specimen S is detected at the higher sensitivity.

In the observation in the culture state of the cultured cells, the cells are maintained in the culture solution. Therefore, in general, there is used an inverted microscope for observing light emission from a bottom surface side of a container in which the cells are accommodated. The method of measuring a Raman scattered light according to the first embodiment of the present disclosure is especially suitable for the case where similarly to the case of the inverted microscope, the Raman scattered light emitted from the cultured cell held in the culture state is detected from the bottom surface side of the culture container.

3. Container for Raman Scattered Light Measurement Specimen

The container 1 for a Raman scattered light measurement specimen according to the second embodiment of the present disclosure includes the space E in which the specimen S is accommodated. As described above, in this case, the sheet member 2 made of the material different from the base material of the bottom surface 11 in the space E is provided on the bottom surface 11 in the space E.

It is noted that the present disclosure can adopt the following constitutions as well.

(1) A method of measuring a Raman scattered light, including radiating an exciting light to a specimen on a sheet member made of a material different from a material of an accommodating section and disposed within the accommodating section, thereby detecting a Raman scattered light.

(2) The method of measuring a Raman scattered light described in the paragraph (1), further including providing the sheet member made of a material different from a base material of a bottom surface of the accommodating section on the bottom surface prior to the detection.

(3) The method of measuring a Raman scattered light described in the paragraph (1) or (2), in which the specimen is a living cell.

(4) The method of measuring a Raman scattered light described in the paragraph (3), further including accommodating of the specimen in which the living cell is cultured on the surface of the sheet member.

(5) The method of measuring a Raman scattered light described in any one of the paragraphs (1) to (4), in which the sheet member is made of at least one or more kinds of resins selected from the group consisting of an acrylic resin, an olefin system resin, and a silicon system resin each of which does not contain therein a benzene ring.

(6) The method of measuring a Raman scattered light described in any one of the paragraphs (1) to (4), in which the sheet member contains therein at least one or more kinds of materials selected from the group consisting polysaccharide, a sugar chain, and a fat.

(7) The method of measuring a Raman scattered light described in any one of the paragraphs (1) to (4), in which the sheet member is made of a gel-like material.

(8) The method of measuring a Raman scattered light described in the paragraph (7), in which the gel-like material is a protein composing an extracellular matrix.

(9) The method of measuring a Raman scattered light described in any one of the paragraphs (5) to (7), in which a thickness of the sheet member is equal to or larger than 0.5 mm.

(10) A container for a Raman scattered light measurement specimen, including:

an accommodating section in which a specimen is accommodated; and a sheet member made of a material different from a base material of a bottom surface of the accommodating section, and provided on the bottom surface.

4. EXAMPLES

Example 1

(4-1) Measurement of Raman Scattered Light Derived from Container for Specimen

In Example 1, the measurement of the Raman scattered light derived from the container for a specimen was carried out, and the intensity of the Raman spectrum in a change in a distance between the objective lens and the bottom surface of the container for a specimen was verified. A container made of polystyrene which is generally used in cell culture experiments or the like was used as the container for a specimen. The focal point of the objective lens was set up to 2.0 mm at intervals of 0.5 mm from the container bottom surface (0 mm) Also, in each of the positions, the exciting light having the wavelength of 785 nm was radiated, and the Raman scattered light emitted from the container bottom surface was measured.

Figure 6A:
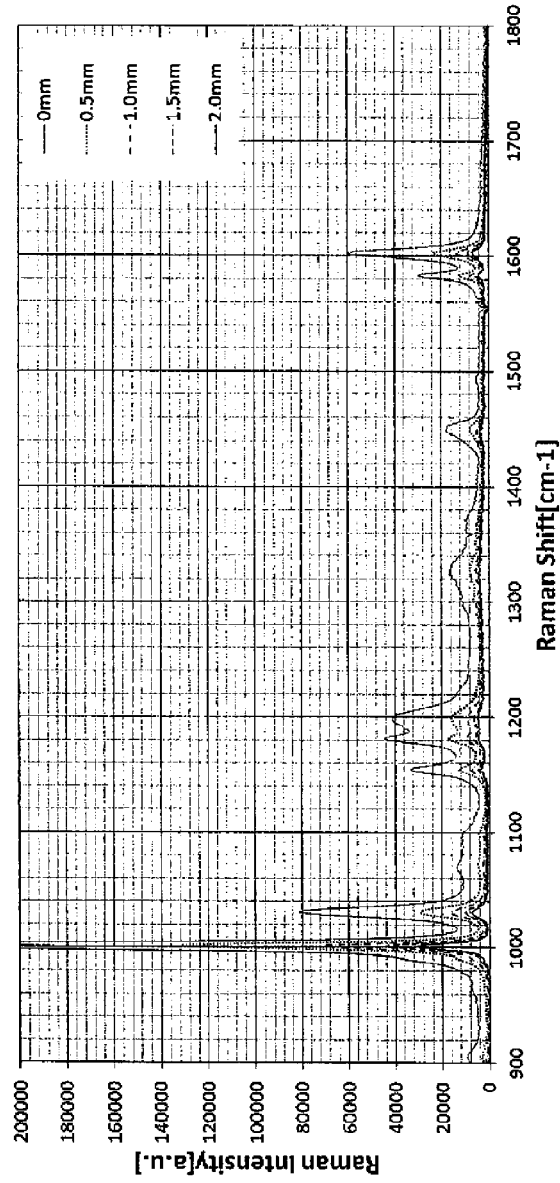
FIGS. 6A, 6B, and 6C are respectively graphs showing results of measurements of a Raman scattered light derived from a container for a specimen in Example 1 of the first embodiment.
Figure 6C:
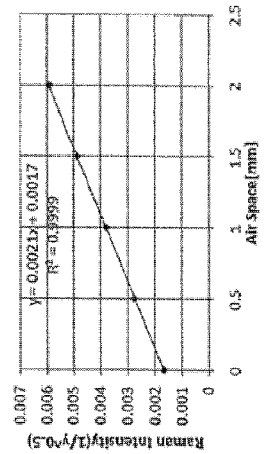
Figure 6B:
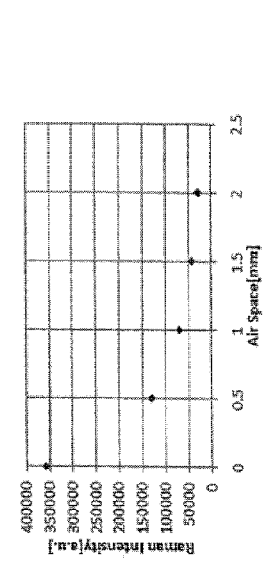

FIG. 6A shows a Raman spectrum derived from the container for a specimen measured in Example 1. In FIG. 6A, an axis of abscissa represents a wavelength (Raman shift) of the measured light, and an axis of ordinate represents an intensity of the Raman scattered light in each of the wavelengths. Also, FIGS. 6B and 6C show intensities of the Raman scattered light in the Raman shift of 1001.36 $cm^{-1}$, respectively. In FIGS. 6B and 6C, an axis of ordinate represents the intensity in the wavelength of 1001.36 $cm^{-1}$ of the Raman spectrum, and an axis of abscissa represents the position of the focal point of the objective lens.

In the spectrum derived from the container for a specimen (refer to FIG. 6A), in the wavelength of 1001.36 $cm^{-1}$ in which the highest intensity was measured, as shown in FIG. 6B, when the focal point of the objective lens was moved from the container bottom surface (0 mm) by 0.5 mm, the intensity of the Raman scattered light was reduced to about ⅓. When the focal point of the objective lens was further moved by 1.0 mm, the intensity of the Raman scattered light was reduced to about ⅕. In Example 1, it was shown that the container for a specimen and the focal point of the objective lens are made away from each other, whereby the intensity of the Raman scattered light derived from the container for a specimen as the object of the measurement is reduced. In addition, it became obvious that a relationship between the distance to the container bottom surface, and the intensity of the Raman scattered light in the wavelength of 1001.36 $cm^{-1}$ is inversely proportional to the square of the distance (refer to FIG. 6C).

Example 2

(4-2) Change in Intensity of Raman Scattered Light Derived from Container for Specimen Due to Installation of Sheet Member (Collagen Gel)

In Example 1, it was shown that the intensity of the Raman scattered light derived from the container for a specimen as the object of the measurement is reduced as the focal point of the objective lens is made more away from the bottom surface of the container for a specimen. Then, the sheet member was studied, which was installed on the container bottom surface, for holding the specimen in the suitable position of the focal point of the objective lens which position was made away from the bottom surface of the container for a specimen.

In Example 2, the same container made of polystyrene as that in Example 1 was used as the container for a specimen, and a collagen gel was used in the sheet member. Amounts of 0.5 ml, 1.0 ml, and 2.0 ml of collagen liquid solution (the thicknesses of the gel to be formed were about 0.5 mm, about 0.1 mm, and about 2.0 mm, respectively) were dropped to the container for a specimen to cause the collagen gel to adhere to the container for a specimen. The exciting light having the wavelength of 785 nm was radiated to the sheet member in order to measure the Raman scattered light. Even in the case of the collagen gel having any of those thicknesses, the focal point of the objective lens was focused on the collagen gel surface (sheet member surface). That is to say, the distance from the collagen gel surface to the objective lens is constant in Example 2.

Figure 7A:
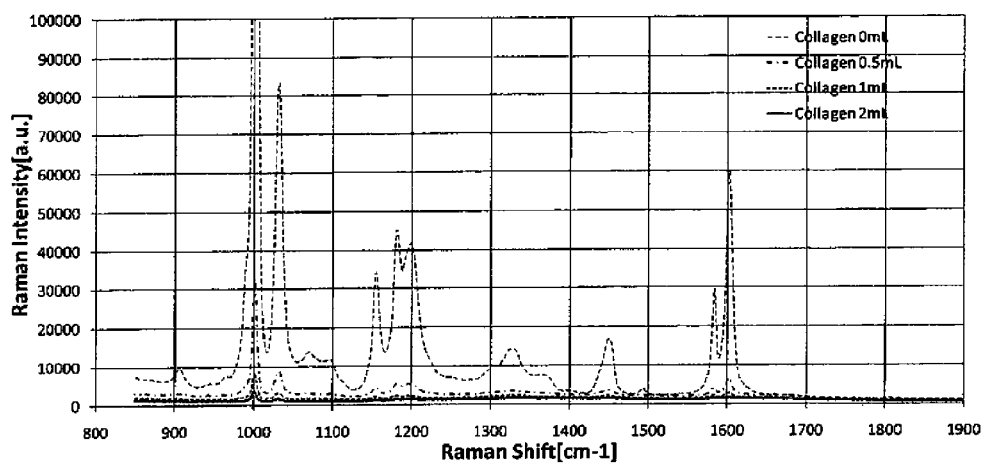
FIGS. 7A and 7B are respectively graphs showing changes in an intensity of the Raman scattered light derived from the container for a specimen due to installation of a sheet member (collagen gel) in Example 2 of the first embodiment.
Figure 7B:
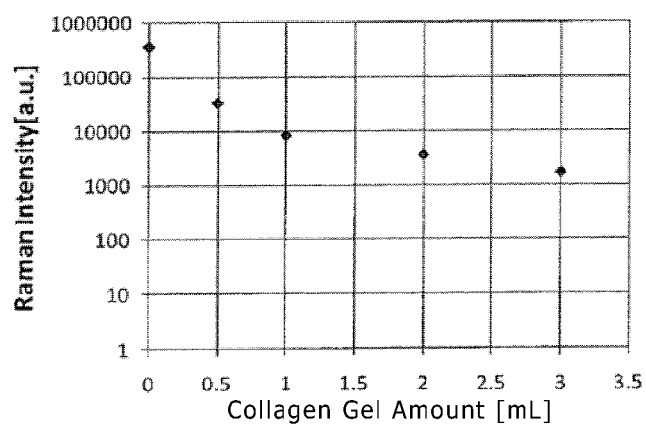

FIGS. 7A and 7B show measurement results in Example 2. FIG. 7A shows a Raman spectrum measured in each of the containers for a specimen. In FIG. 7A, an axis of abscissa represents the wavelength (Raman shift) of the measured light, and an axis of ordinate represents the intensity of the Raman scattered light in each of the wavelengths. FIG. 7B shows the intensity of the Raman scattered light in the wavelength of 1001 $cm^{-1}$. In FIG. 7B, an axis of ordinate represents the intensity of the Raman scattered light in the wavelength of 1001 $cm^{-1}$, and an axis of abscissa represents a collagen gel amount.

In the case of the container for a specimen in which no collagen gel was provided (Collagen 0 ml in FIG. 7A), similarly to the case of Example 1, the high intensity was recognized in the wavelength of 1001 $cm^{-1}$. On the other hand, in the case of the container in which 0.5 ml of the collagen gel (the thickness of the gel was about 0.5 mm), the intensity of the Raman scattered light in the wavelength of 1001 $cm^{-1}$ was reduced about 1/10 (refer to FIG. 7B) as compared with the case where no collagen gel was provided. In addition, when 1.0 ml of the collagen gel was used, the intensity of the Raman scattered light in the wavelength of 1001 $cm^{-1}$ was reduced about 1/50 (refer to FIG. 7B) as compared with the case where no collagen gel was provided. Those measurement results showed that when the collagen gel is provided on the bottom surface of the container for a specimen, and the focal point of the objective lens is focused on the surface of the sheet member made of collagen gel instead of the bottom surface of the container for a specimen, the intensity of the Raman scattered light derived from the container for a specimen is reduced depending on the thicknesses of the sheet member.

Example 3

(4-3) Measurement of Raman Scattered Light from Specimen in Container for Specimen After Installation of Sheet Member (Collagen Gel)

In Example 3, it was verified whether or not the reduction, in the intensity of the Raman scattered light derived from the container for a specimen due to the installation of the sheet member, which was recognized in Example 2 was effective in the measurement of the Raman scattered light derived from the specimen. Similarly to the case of Examples 1 and 2 described above, the container made of polystyrene was used as the container for a specimen. The collagen gel was used in the sheet member similarly to the case of Example 2, and the thickness of the gel was set to about 0.5 mm. A hepatic cell was used as the specimen and was cultured on the sheet member by utilizing the known method. A container for a specimen in which no collagen gel was laminated was also prepared as an object of comparison, and the hepatic cell was cultured on the container bottom surface (on the base material made of polystyrene). The measurement of the Raman scattered light was carried out in a state in which the hepatic cell was cultured. In a phase of the measurement, the exciting light having the wavelength of 785 nm was radiated either to the hepatic cells cultured in the containers or to portions in which the cells were absent in the containers, and the focal point of the objective lens was focused on each of the hepatic cells.

Figure 8A:
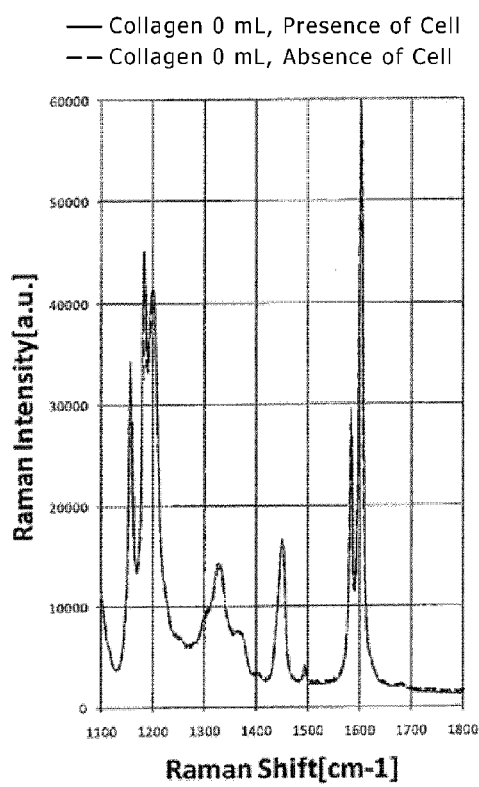
FIGS. 8A and 8B are respectively graphs showing results of measurements of the Raman scattered light derived from a specimen in the container for a specimen after the installation of the sheet member (collagen gel) in Example 3 of the first embodiment.
Figure 8B:
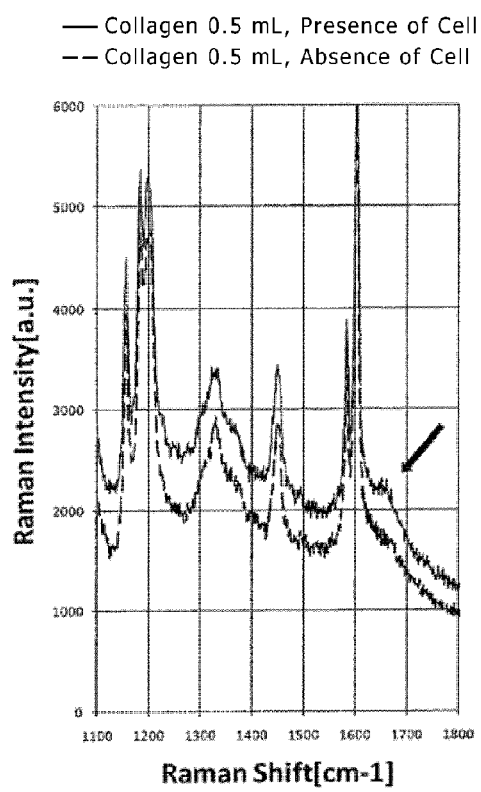

FIGS. 8A and 8B show measurement results in Example 3. In FIGS. 8A and 8B, an axis of abscissa represents the wavelength (Raman shift) of the measured light, and an axis of ordinate represents the intensity of the Raman scattered light in each of the wavelengths. FIG. 8A shows a pattern of the Raman spectra derived from the cell and derived from the bottom surface of the container for a specimen, respectively, in the container for a specimen in which no collagen gel is laminated. The Raman spectrum of a portion indicated by a broken line in which the cell is absent (absence of cell) agreed with the Raman spectrum of a portion indicated by a solid line in which the cell is present (presence of cell). Those measurement results show that when the cell is cultured on the bottom surface of the container for a specimen and the Raman scattered light is measured, the Raman scattered light derived from the cell is not measured at the high sensitivity. On the other hand, as shown in FIG. 8B, in the container for a specimen in which the collagen gel was laminated, when the Raman scattered light from a portion in which the cell is present (presence of cell) was measured, the Raman spectrum whose pattern was different from that of the Raman spectrum from a portion in which the cell is absent (absence of cell) was measured. That is to say, there was the Raman scattered light which is recognized only when the portion in which the cell is present is measured (indicated by an arrow mark in the figure) . That is to say, the Raman scattered light concerned is the Raman scattered light derived from the cell. From the above measurement results, it was shown that when the collagen gel is used as the sheet member in the bottom surface of the container, the detection of the Raman scattered light derived from the container is suppressed and thus the Raman scattered light derived from the specimen can be measured at the high sensitivity without being impeded by the Raman scattered light derived from the sheet member.

Example 4

(4-4) Change in Intensity of Raman Scattered Light Derived from Container for Specimen Due to Installation of Sheet Member (PDMS)

Although in Examples 2 and 3, the collagen gel was used as the sheet member, the sheet member made of another material was also studied. In Example 4, polydimethylsiloxane (PDMS) as one of the synthetic resins was used as the sheet member. The container made of polystyrene was used as the container for a specimen similarly to the case of Examples 1 to 3 described above. Also, PDMS was polymerized within the container, and was laminated as the sheet member on the bottom surface of the container. With regard to the container for a specimen in which PDMS was not laminated, and the containers for a specimen in which the PDMS materials having the thickness of six stages from 0.4 mm to 2.84 mm were laminated, respectively, the exciting light having the wavelength of 785 nm was radiated thereto, thereby measuring the Raman scattered lights emitted therefrom. The focal point of the objective lens was focused on the PDMS surface (the surface of the sheet member). That is to say, a distance from the PDMS surface (the surface of the sheet member) to the objective lens is constant in Example 4.

Figure 9:
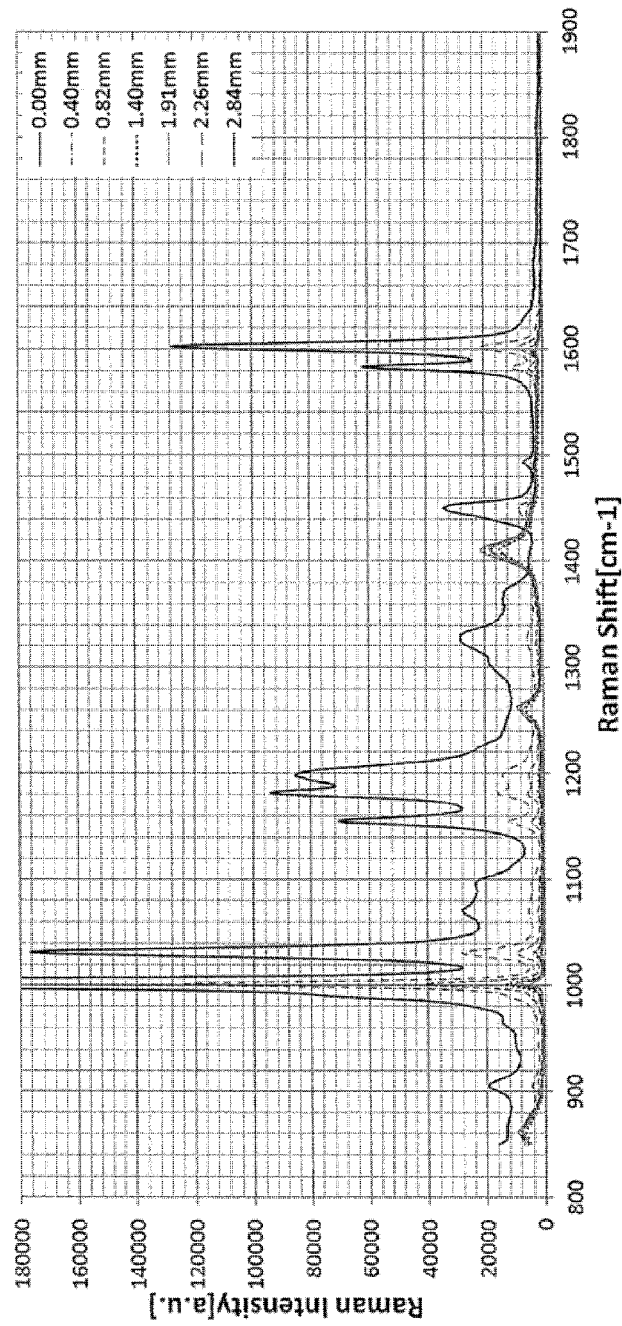
FIG. 9 is a graph showing changes in an intensity of the Raman scattered light derived from the container for a specimen due to installation of a sheet member (PDMS) in Example 4 of the first embodiment.

FIG. 9 shows the Raman spectra measured in Example 4. In FIG. 9, an axis of abscissa represents the wavelength (Raman shift) of the measured light, and an axis of ordinate represents the intensity of the Raman scattered light in each of the wavelengths. Since the container was made away from the focal point of the objective lens as the thickness of PDMS was more increased, the intensity of the Raman spectrum derived from the container was reduced similarly to the case of Examples 1 and 2. On the other hand, the Raman spectrum derived from PDMS was measured in the container in which PDMS was used as the material of the sheet member. However, the intensity of the Raman spectrum derived from PDMS was lower than that of the Raman spectrum derived from the container for a specimen and, for example, the intensity of the Raman scattered light which was measured in the vicinity of the wavelength of 1,400 $cm^{-1}$ was about 20,000 a.u. From the measurement results in Example 4, it was shown that similarly to the case of the collagen gel, PDMS is effective as the sheet member which is installed in the container for a specimen in the measurement of the Raman scattered light.

Example 5

(4-5) Measurement of Raman Scattered Light from Specimen in Container for Specimen After Installation of Sheet Member (PDMS)

In Example 5, it was verified whether or not the reduction, in the intensity of the Raman scattered light derived from the container for a specimen due to the installation of the sheet member, which was recognized in Example 4 was effective in the measurement of the Raman scattered light derived from the specimen. The container made of polystyrene was used as the container for a specimen similarly to the case of Example 4 described above. PDMS was used as the material of the sheet member and a thickness thereof was set to about 0.82 mm. A hair of the human (hereinafter referred to as "a white hair") was used as the specimen. The focal point of the objective lens was focused on the surface of the white hair, and the exciting light having the wavelength of 785 nm was radiated to the white hair accommodated in the container, thereby measuring the Raman scattered light.

Figure 10A:
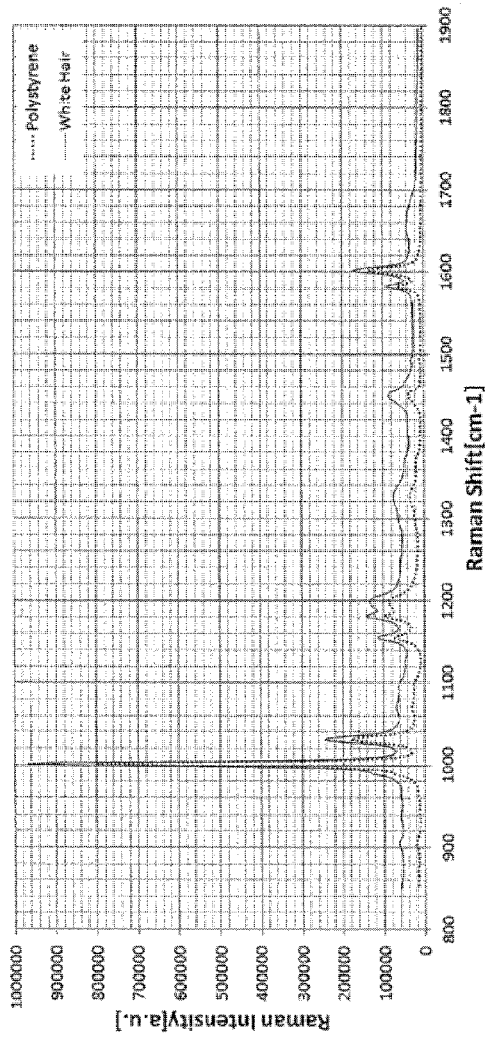
FIGS. 10A and 10B are respectively graphs showing results of measurements of the Raman scattered light derived from a specimen in the container for a specimen after the installation of the sheet member (PDMS) in Example 5 of the first embodiment.
Figure 10B:
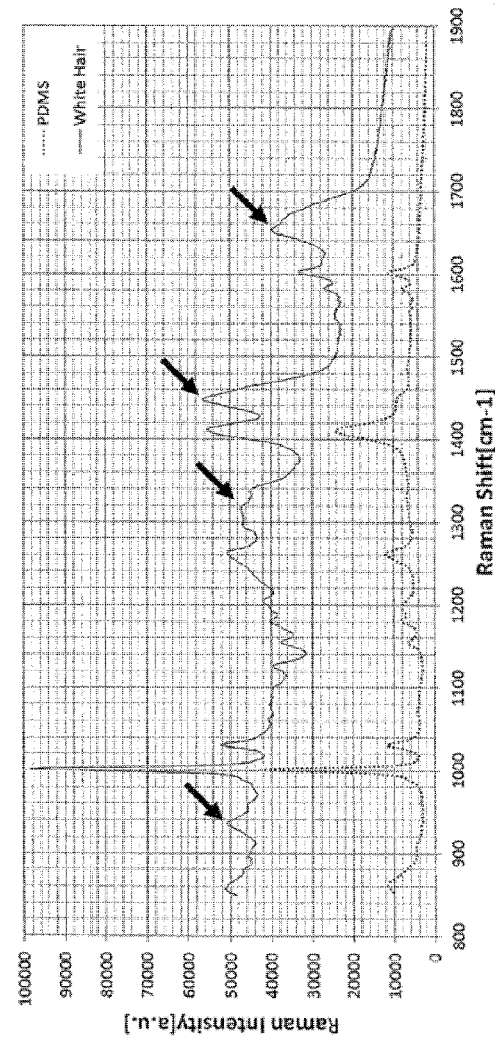

FIGS. 10A and 10B show the measurement results in Example 5. The Raman spectra shown in FIG. 10A is the measurement results in the container for a specimen (Polystyrene) in which the sheet member made of PDMS was not installed. Even when the white hair as the specimen was placed, the pattern of the Raman spectrum which was the same as that of the Raman spectrum measured in a state in which the specimen was not placed was measured. On the other hand, as shown in FIG. 10B, in the container for a specimen in which the sheet member was installed, the Raman spectrum when the measurement was carried out in the state in which the specimen was placed is different in pattern from that when the measurement was carried out only in the container for a specimen, and thus the specific peaks (indicated by arrow marks in the figure) were measured in the phase of the measurement of the specimen. From the measurement results in Example 5, it was shown that when the PDMS is also used as the sheet member in the bottom surface of the container, the detection of the Raman scattered light derived from the container is suppressed and thus the Raman scattered light derived from the specimen can be measured at the high sensitivity without being impeded by the Raman scattered light derived from the sheet member.

In the method of measuring a Raman scattered light according to the first embodiment of the present disclosure, the Raman scattered light derived from the specimen accommodated in the container can be detected at the high sensitivity. From this reason, the method of measuring a Raman scattered light of the first embodiment can be utilized in the measurement of the specimen, such as the cell held in the culture state, which can be used in the measurement only in the state in which it is accommodated in the container. The analysis of the cell held in the culture state is important in the regenerative medical techniques because the degree of the differentiation from the stem cell, for example, can be confirmed, and so forth.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A method of measuring a Raman scattered light, comprising:
   radiating an exciting light to a specimen on a sheet member, wherein the sheet member is disposed within an accommodating section, thereby detecting a Raman scattered light;
   wherein the sheet member is made of a material different than a material of the accommodating section; and
   wherein at least a part of a bottom surface of the accommodating section comprises light permeable material.

2. The method of measuring a Raman scattered light according to claim 1, wherein said sheet member is made of at least one or more kinds of resins selected from the group consisting of an acrylic resin, an olefin system resin, and a silicon system resin each of which does not contain therein a benzene ring.

3. The method of measuring a Raman scattered light according to claim 2, wherein a thickness of said sheet member is equal to or larger than 0.5 mm.

4. The method of measuring a Raman scattered light according to claim 1, wherein said sheet member contains therein at least one or more kinds of materials selected from the group consisting polysaccharide, a sugar chain, and a fat.

5. The method of measuring a Raman scattered light according to claim 1, wherein said sheet member is made of a gel-like material.

6. The method of measuring a Raman scattered light according to claim 5, wherein said gel-like material is a protein composing an extracellular matrix.

7. The method of measuring a Raman scattered light according to claim 1, wherein said specimen is a living cell.

8. The method of measuring a Raman scattered light according to claim 7, further comprising:
   accommodating said specimen in which said living cell is cultured on the surface of said sheet member.

9. A container for a Raman scattered light measurement specimen, comprising:
   an accommodating section in which a specimen is accommodated; and
   a sheet member made of a material different from a base material of a bottom surface of said accommodating section, and provided on said bottom surface of the accommodating section,
      wherein at least part of the bottom surface of the accommodating section comprises light permeable material.

10. The container for a Raman scattered light measurement specimen according to claim 9, wherein said sheet member is made of at least one or more kinds of resins selected from the group consisting of an acrylic resin, an olefin system resin, and a silicon system resin, each of which does not contain therein a benzene ring.

11. The container for a Raman scattered light measurement specimen according to claim 10, wherein a thickness of said sheet member is equal to or larger than 0.5 mm.

12. The container for a Raman scattered light measurement specimen according to claim 9, wherein said specimen is a living cell and said sheet member is configured to culture said living cell on a surface of said sheet member.

13. A system for measuring a Raman scattered light comprising:
   a container for a Raman scattered light measurement specimen comprising:
      an accommodating section in which a specimen is accommodated and of which at least part of a bottom surface comprises a light permeable material; and
      a sheet member made of a material different from a base material of said bottom surface of said accommodating section, wherein the sheet member is provided on said bottom surface of said accommodating section;
   a light source configured to radiate an exciting light to said specimen accommodated in said container; and
   a detector configured to detect a Raman scattered light.

14. A system for measuring a Raman scattered light according to claim 13, wherein said light source and said detector are arranged under said container.

15. A system for measuring a Raman scattered light according to claim 14, wherein said specimen is a living cell and said sheet member is configured to culture said living cell on a surface of said sheet member.

* * * * *